(12) United States Patent
Steiner

(10) Patent No.: US 6,514,465 B2
(45) Date of Patent: Feb. 4, 2003

(54) APPARATUS FOR RECEIVING AN OBJECT, ARRANGEMENT FOR TRANSPORTING AND FOR RECEIVING AND OBJECT AND METHOD FOR THEIR OPERATION

(75) Inventor: Edwin Steiner, Alpthal (CH)

(73) Assignee: Tecan Trading AG, Mannedorf (CH)

( * ) Notice: Subject to any disclaimer, the term of this patent is extended or adjusted under 35 U.S.C. 154(b) by 0 days.

(21) Appl. No.: 09/740,192

(22) Filed: Dec. 18, 2000

(65) Prior Publication Data
US 2001/0018031 A1 Aug. 30, 2001

(30) Foreign Application Priority Data
Dec. 21, 1999 (EP) .............................. 99811180

(51) Int. Cl.[7] .............................. B01L 9/00; B23Q 3/00; A47G 29/00
(52) U.S. Cl. .......................... 422/104; 422/99; 422/58; 422/63; 422/65; 269/254 CS; 269/303; 269/305; 248/678; 248/346.03
(58) Field of Search ............................ 356/244; 422/65, 422/99, 104; 436/47, 48; 211/41.1; 81/300; 269/254 CS, 303, 305; 248/678, 346.03

(56) References Cited

U.S. PATENT DOCUMENTS

| 4,621,797 A | * | 11/1986 | Ziegenfuss | 269/238 |
| 4,776,822 A | * | 10/1988 | Dougherty et al. | 29/423 |
| 4,784,377 A | * | 11/1988 | Woodward | 269/21 |
| 4,908,995 A | * | 3/1990 | Dougherty et al. | 451/28 |
| 5,591,402 A | * | 1/1997 | Jones | 422/65 |
| 5,599,500 A | * | 2/1997 | Jones | 422/100 |
| 5,845,555 A | * | 12/1998 | Dawley | 83/467.1 |
| 5,961,107 A | * | 10/1999 | Morghen | 269/100 |
| 6,071,748 A | * | 6/2000 | Modlin et al. | 250/459.1 |
| 6,323,035 B1 | * | 11/2001 | Kedar et al. | 414/277 |

FOREIGN PATENT DOCUMENTS

| WO | WO-97-11352 | * | 3/1997 | G01N/21/01 |
| WO | WO 99/04228 | * | 1/1999 | |

OTHER PUBLICATIONS

Encyclopedia Britannica Online Dictionary http://www.search.eb.com Definitions for "branch," "end," "fin," "lever," and "oblique".*

* cited by examiner

Primary Examiner—Jill Warden
Assistant Examiner—Elizabeth Quan
(74) Attorney, Agent, or Firm—Notaro & Michalos P.C.

(57) ABSTRACT

A support surface (3) is bordered on at least two sides by fins while mounted at an opposite corner is a clamping device comprising a slide (6) which can be drawn back from a starting position against the force of a coil spring (9) and which has a clamping plate (10) which has a clamping surface facing the diagonally opposite corner. When a microtitre plate is set down on the support surface (3) by means of a gripper, a lever (12) of the clamping device (5) is pressed down by a gripper arm and the clamping plate (10) is drawn back from a starting position by the action of a thrust surface (15) on the underside of the lever (12) on a sliding projection (11) of the slide (6) and said clamping plate is then moved forwards again to said starting position when the gripper is raised, so that it clamps the microtitre plate against the fins and holds it in a defined position.

9 Claims, 6 Drawing Sheets

APPARATUS FOR RECEIVING AN OBJECT, ARRANGEMENT FOR TRANSPORTING AND FOR RECEIVING AND OBJECT AND METHOD FOR THEIR OPERATION

FIELD OF THE INVENTION

The invention relates to an apparatus for receiving an object, in particular a microtitre plate, an arrangement for transporting and for receiving such an object and a method for their operation and can be used in particular in the area of laboratory equipment for chemical, biological and medical investigations.

PRIOR ART

It is known that microtitre plates and the like can be placed on support surfaces and then processed, for example samples being delivered into the individual wells or removed from them by means of an automatic pipetting apparatus. The microtitre plate must be very accurately positioned for this purpose.

Thus, U.S. Pat. No. 5,592,289 discloses an apparatus of the generic type in which the support surface rests on the base of a rectangular depression, with compression springs which are arranged at two side walls at right angles to one another and which press the microtitre plate against the two respective opposite side walls, which act as a stop, and thus position said microtitre plate. In another apparatus described in the same publication, the support surface is arranged on a displaceable slide. After the microtitre plate has been deposited, said slide is pushed by a compression spring against a stop which is formed by three stationary pins engaging short oblique slots in the slide. The microtitre plate reaches the stop formed by the pins at an earlier time and is thus pushed against a clamping part elastically held on the slide and is clamped between said clamping part and the pins.

In the case of the luminescence analyzer described in WO-A-99/04 228 a sample support is received by an orifice in a slide and is pressed by two clamping parts which can move at right angles to one another and which, when the slide is moved in, are pushed free from a stop and by spring force against those sides of the sample support which are at right angles to one another, against the respective opposite edges of the orifice and is thereby positioned.

In the apparatuses described, the clamping parts are either in the way when the microtitre plate is deposited and impair the reliability of deposition and positioning thereof, or they have to be separately controlled in a relatively complicated manner.

SUMMARY OF THE INVENTION

It is the object of the invention further to develop an apparatus which receives an object, such as a microtitre plate, so that it is accurately positioned between a stop and a displaceable clamping part and is held in its position in such a way that, when the object is deposited and received, the clamping part can be pulled back by pressure from above so that it does not hinder the process. This object is achieved by the features in the characterizing clause of claim 1.

The advantages achieved by the invention are in particular that the object can be brought safely and reliably into an exactly defined position and held there with moderate control effort. There, it can be subjected to operations for the successful performance of which accurate positioning is essential.

The design of the apparatus according to the invention is very simple and requires only a few moving parts. Particularly advantageous is the combination of an apparatus according to the invention with a gripper which is suitable for transporting and setting down the object and at the same time controlling the apparatus, to give an arrangement according to the invention for transporting and for receiving an object according to claim 10. Such an arrangement permits operation according to the method of the invention according to claim 11, in which the positioning of the object is initiated simultaneously with the setting down thereof, without additional measures and further control effort being required.

BRIEF DESCRIPTION OF THE DRAWINGS

The invention can be explained in more detail below with reference to Figures, which constitute only one embodiment.

FIG. 7b shows a plan view of the arrangement according to FIG. 7a.

DESCRIPTION OF THE PREFERRED EMBODIMENTS

Figure 1:
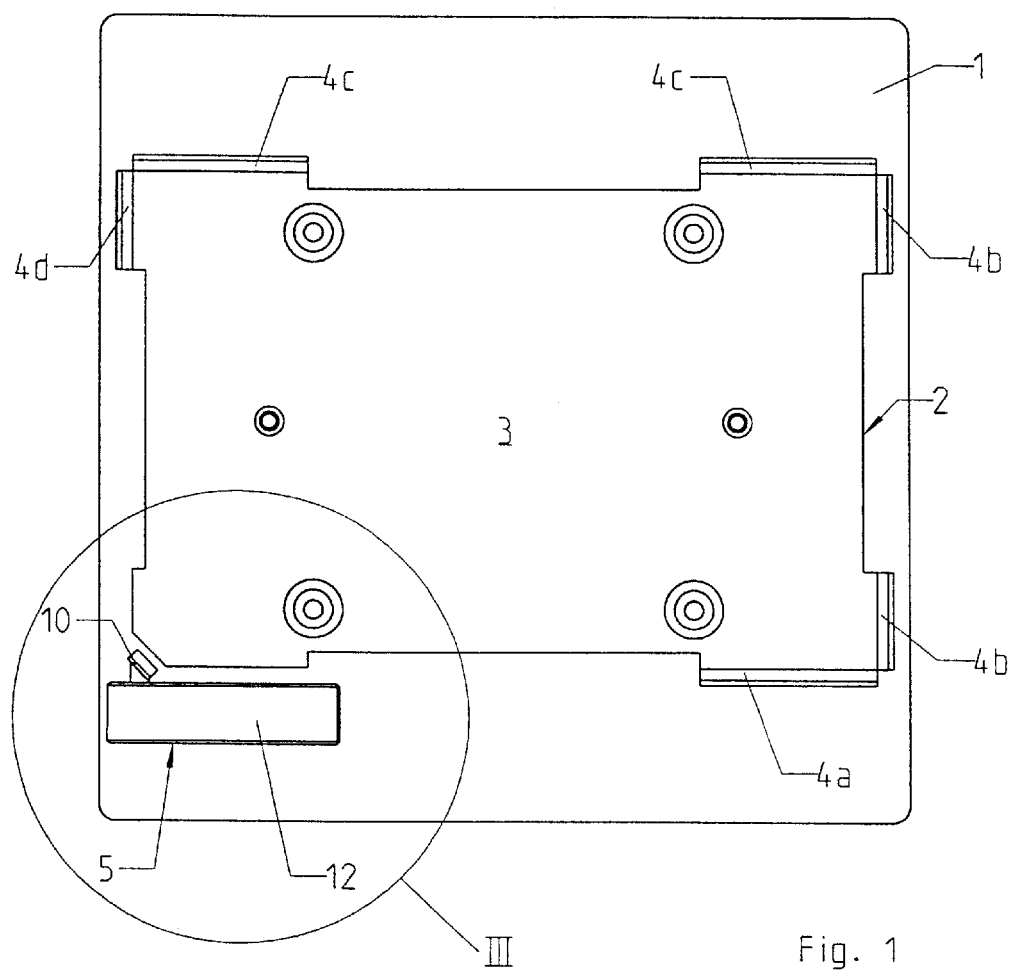
FIG. 1 shows a plan view of an apparatus according to the invention.

Arranged on, for example, a laboratory apparatus is a horizontal baseplate 1 to which a flat position plate 2 is screwed, which forms a flat, essentially rectangular support surface 3. The latter is bordered by projecting fins 4a,b,c,d, some of which are interrupted in the middle and of which the fins 4b,c form a stop which limits the displacement of an object placed on the support surface 3 and having in particular a rectangular contour, in two directions at right angles to one another, in each case on one side, i.e. outwards.

Figure 2:
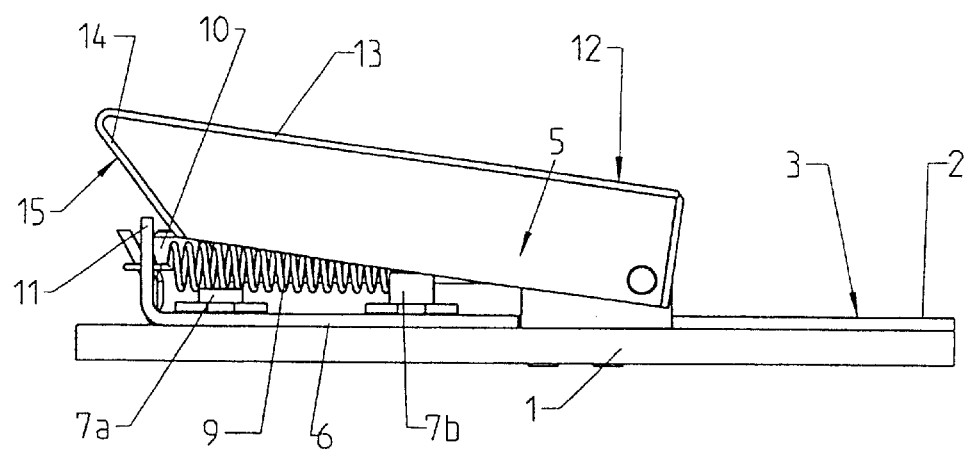
FIG. 2 shows, on a larger scale, a side view of a clamping device of the apparatus according to the invention.
Figure 3:
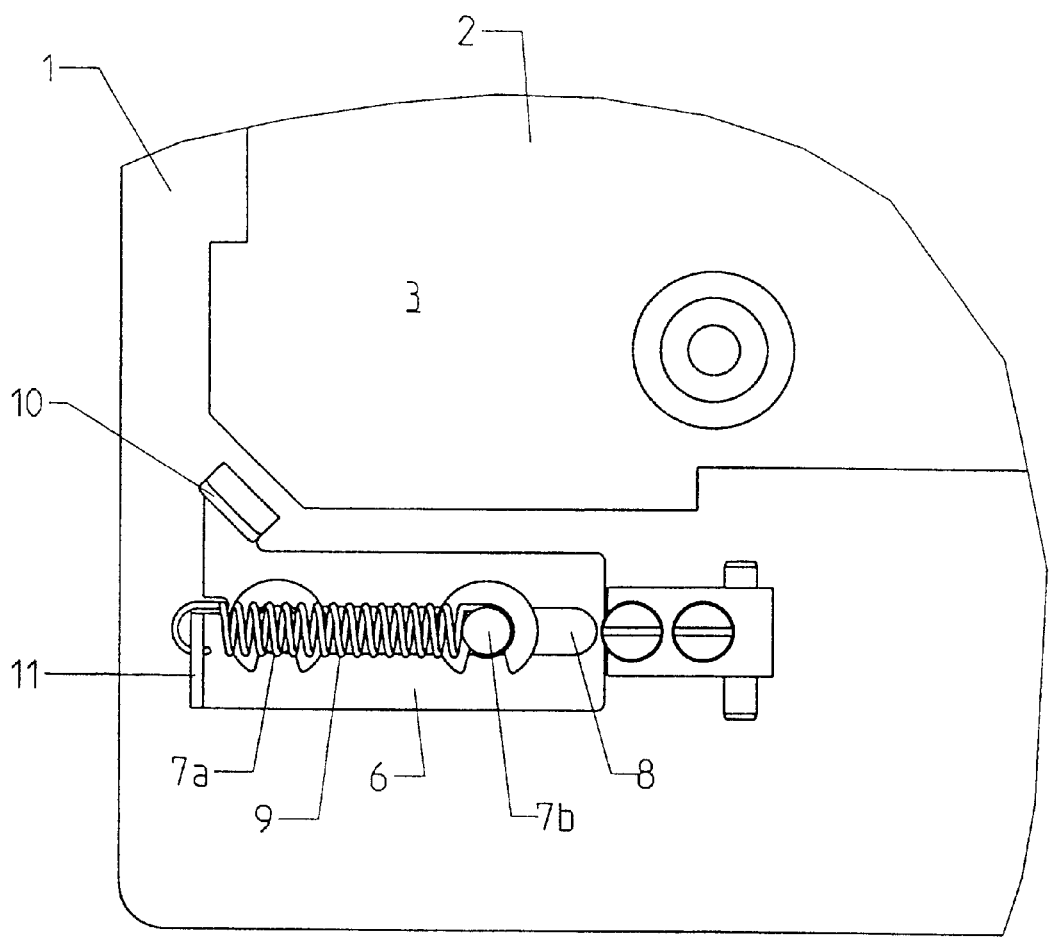
FIG. 3 shows, on a larger scale, a plan view of a cut-out III in FIG. 1, a part of the clamping device having been removed.

A clamping device 5 is arranged slightly outside that corner of the support surface 3 which is opposite the corner framed by the fins 4b,c. Said clamping device comprises (FIGS. 2, 3) a plate-like slide 6 which is guided on two bolts 7a,b, which project through a central slot 8, in such a way that it is longitudinally displaceable parallel to the fin 4c and at right angles to the fin 4b. By means of a tensioned coil spring 9 which is anchored to the rear bolt 7b, the slide 6 is held in a starting position in which the end of slot 8 is against the front bolt 7*a*. The coil spring 9 holds the slide 6 under an initial tension in the starting position too, so that it can be pulled back from said position only by the action of force. The slide 6 carries, at one end, a clamping plate 10 which is laterally offset with respect to the support surface 3, is directed perpendicularly upwards and forms an oblique clamping surface pointing towards the corner framed by the fins 4*b,c*. It is thus suitable for exerting on the object to be held a force which presses said object against both fins 4*b,c* acting as stops, although the force exerted by the coil spring 9 on the slide 6 is directed precisely towards the fin 4*b* and is parallel to the fin 4*c*.

Furthermore, the slide 6 has, at the same end, an upward-projecting sliding extension 11 which is arranged in the extension of the slot 8. Said sliding extension operates with a lever 12 which is mounted slightly outside the opposite end of the slide 6 in a manner such that it is pivotable about a horizontal axle connected to the baseplate 1. The lever 12 has an approximately horizontal cover plate 13 and a thrust plate 14 which is curved downward and makes an acute angle with the cover plate 13 and whose underside forms a thrust surface 15 which acts on the sliding extension 11.

If the lever 12 is now turned by a force acting on the cover plate 13 and directed downwards, the thrust surface 15 acts on the sliding extension 11 in such a way that the slide 6 is displaced and, including the clamping plate 10, is pulled back from the starting position with extension of the coil spring 9. Once the action of the force ceases, the slide 6 with the clamping plate 10 is moved back to the starting position by the coil spring 9, while the lever 12 is raised by the action of the sliding extension 11 on the thrust surface 15. Instead of the sliding extension 11, a differently formed contact part, e.g. a roller, may also be applied.

Figure 4A:
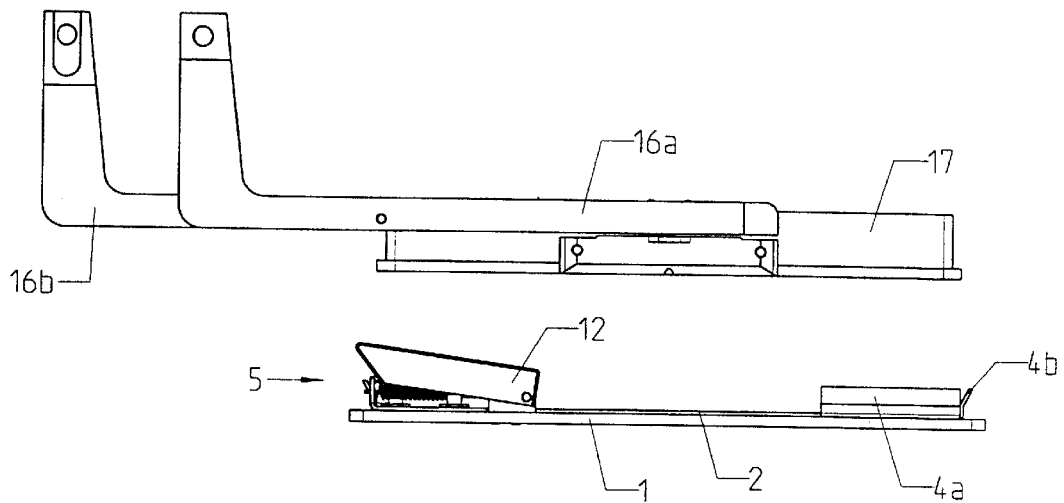
FIG. 4a shows a side view of an arrangement according to the invention during a first phase of the method according to the invention.
Figure 4B:
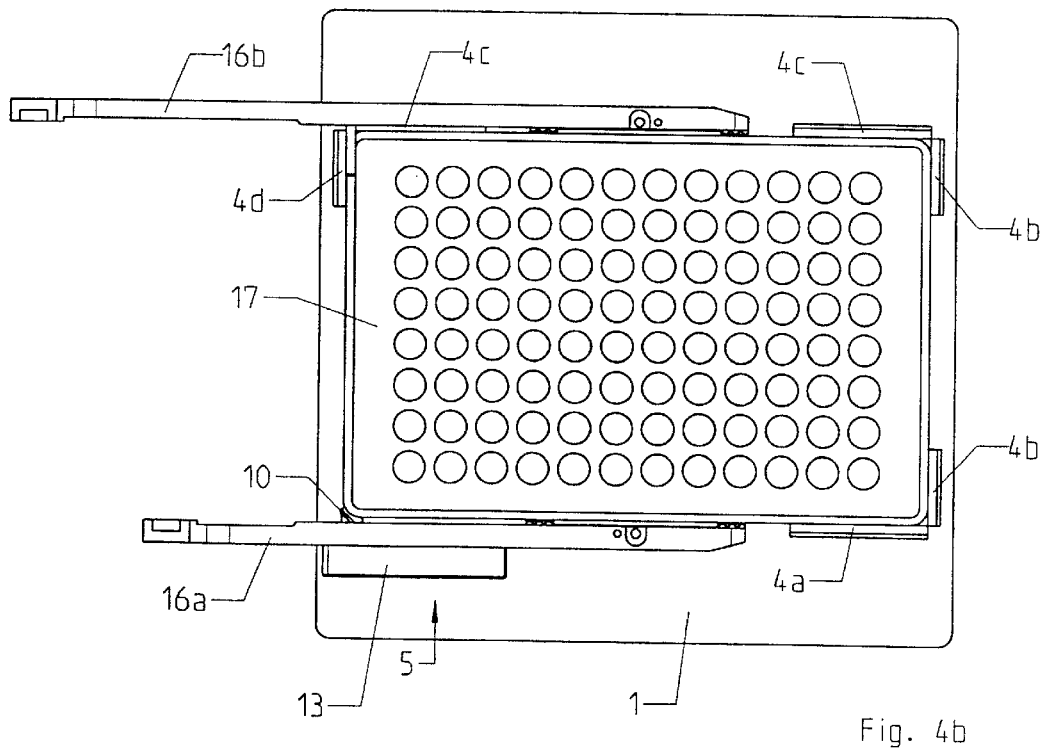
FIG. 4b shows a plan view of the arrangement according to FIG. 4a, FIG. 5a shows a side view of the arrangement according to the invention during a second phase of the method according to the invention.
Figure 5A:
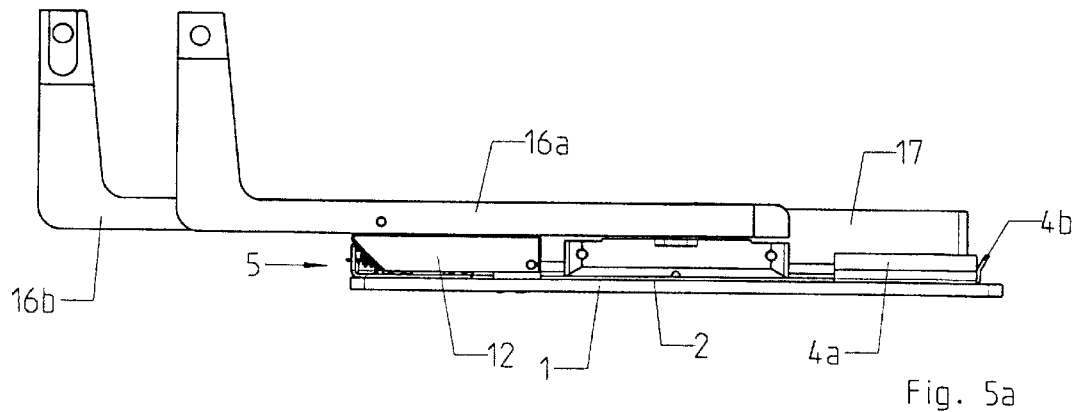
FIG. 5b shows a plan view of the means according to FIG. 5a, FIG. 6a shows a side view of the arrangement according to the invention during a third phase of the method according to the invention.
Figure 5B:
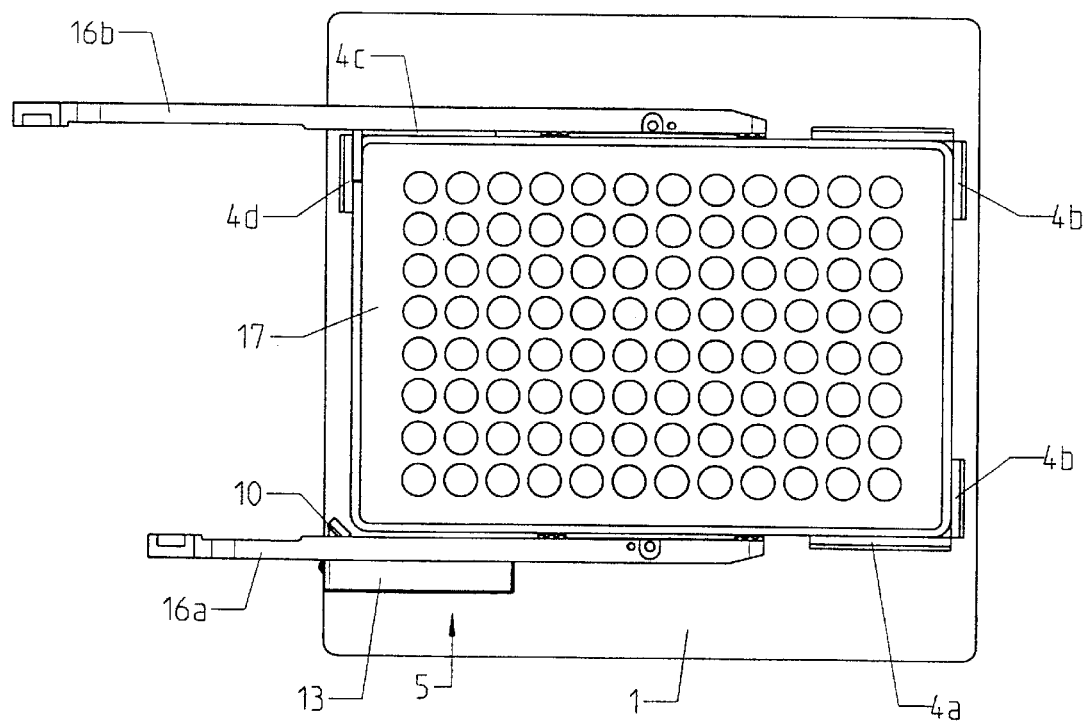

The arrangement according to the invention additionally has (FIGS. 4*a,b*–7*a,b*) a gripper having two parallel arms 16*a,b* which together can be raised and lowered and can be moved parallel to the plane of the support surface 3 and towards and away from one another. The gripper arms 16*a,b* hold, for example, a microtitre plate 17 between them and transport it to a position above the support surface 3 (FIGS. 4*a,b*). Thereafter, the gripper arms 16*a,b* with the microtitre plate 17 are lowered and the latter is placed on the support surface 3 (FIGS. 5*a,b*). During the last part of this movement, the right gripper arm 16*a* presses on the cover plate 13 which, in a manner described above, causes the clamping plate 10 to be drawn back from the starting position, so that it is out of the way and does not hinder the deposition of the microtitre plate 17.

Figure 6A:
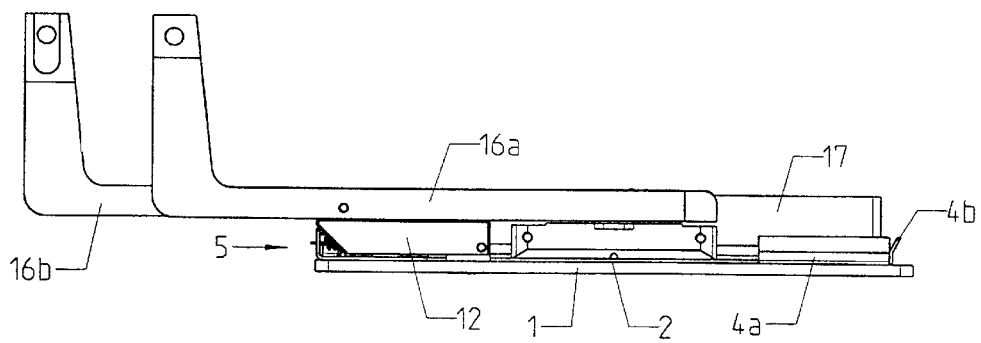
FIG. 6b shows a plan view of the arrangement according to FIG. 6a, FIG. 7a shows a side view of the arrangement according to the invention during a fourth phase of the method according to the invention
Figure 6B:
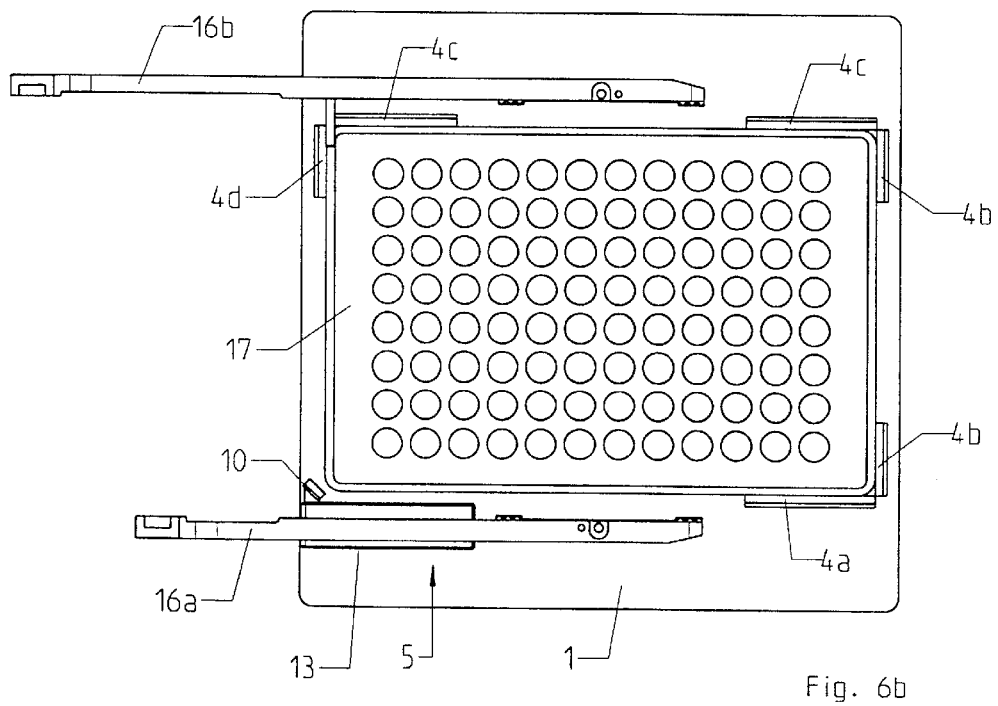
Figure 7A:
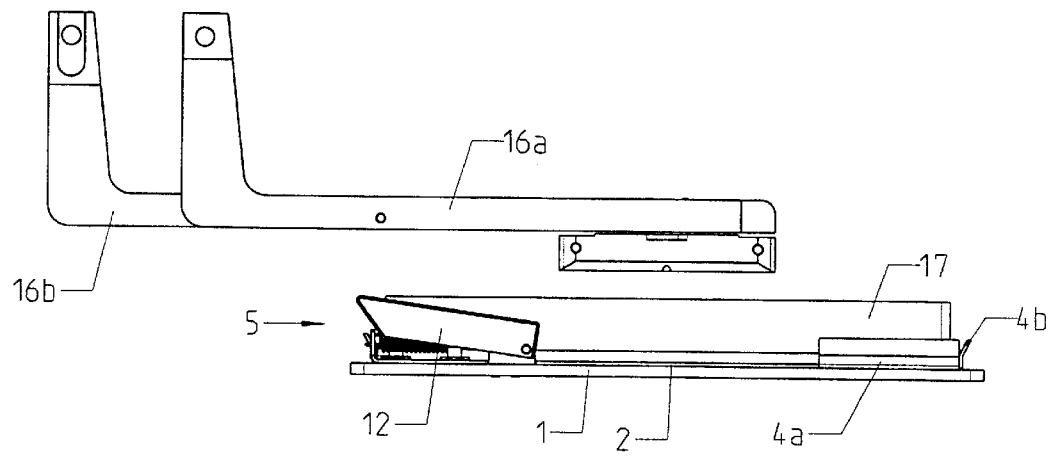
Figure 7B:
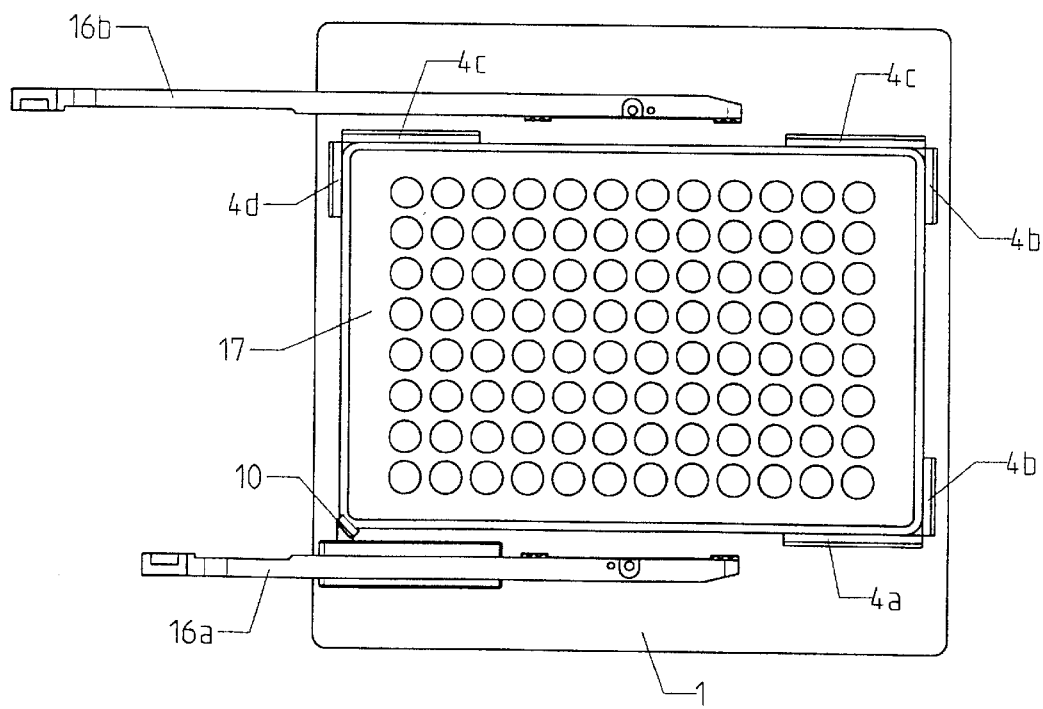

Thereafter, the gripper arms 16*a,b* are moved sidewards and outwards and thus detached from the microtitre plate 17 (FIGS. 6*a,b*). Finally, they are raised, with the result that the clamping plate 10 moves towards the starting position in a manner likewise described above, until it abuts the microtitre plate 17 and, if required, pushes it towards the fins 4*b,c* acting as stops and presses it against them. The microtitre plate 17 has then been brought into a position exactly defined by the fins 4*b,c* and has been clamped between them and the clamping plate 10. It is now possible to perform an operation which requires an accurately controlled position of the microtitre plate 17, such as, for example, the withdrawal of samples from the wells thereof or the delivery of samples into said wells by means of an automatically controlled pipetting apparatus. After the end of the procedure, the microtitre plate 17 can be picked up again in a corresponding manner and transported away.

The clamping device need not be separately controlled but is to a certain extent actuated additionally by the gripper arm 16*a,b*. It is a purely passive mechanical element and can therefore be very simply designed and correspondingly cheap.

List of Reference Symbols

1 Baseplate
2 Positioning plate
3 Support surface
4*a,b,c,d* Fins
5 Clamping device
6 Slide
7*a,b* Bolts
8 Slot
9 Coil spring
10 Clamping plate
11 Sliding extension
12 Lever
13 Cover plate
14 Thrust plate
15 Thrust surface
16*a,b* Gripper arms
17 Microtitre plate

What is claimed is:

1. An apparatus for receiving and positioning an object, the apparatus comprising: a base plate (1) with a support surface thereon (3) and a stop located on one side of the support surface (3), the stop limiting displacement of the object when positioned said support surface (3); a clamping device mounted on said base plate having a slide (6) with a clamping plate (10) for exerting a force on the object, the clamping plate (10) facing the stop and being mounted to be linearly drawn back together with the slide (6) relative to the stop against an initial tension; the clamping device further comprising a lever (12) pivotably connected at a first end to the base plate (1) by an axle that extends parallel to the support surface (3) and the stop, on a second end the lever comprises a downwardly facing, oblique thrust surface (15) which is in sliding contact with an upwardly projecting, sliding extension (11) of the slide (6), so that pressing down the lever (12) on its second end pivots the lever around the axle, the oblique thrust surface (15) sliding on the sliding extension (11) and causing the slide (6) and the clamping plate (10) to slide parallel to support surface away from the stop and thereby releasing the object.

2. The apparatus of claim 1, wherein the stop comprises two fins (4*b*,4*c*) arranged at an edge of the support surface (3) and oriented at right angles to one another for limiting displacement of the object in two directions perpendicularly oriented to one another the axle extending parallel to one of said fins.

3. The apparatus of claim 2, wherein the clamping plate (10) is an oblique surface each of the fins.

4. The apparatus of claim 3, wherein the clamping plate forms an acute angle of about 45 degrees.

5. The apparatus of claim 2, wherein the slide (6) is arranged at an edge of the support surface (3) in such a way that the slide moves parallel to one of the fins (4*b*,4*c*).

6. The apparatus of claim 1, further comprising an object on the support surface wherein the object is a microtitre plate (17).

7. An arrangement for transporting and receiving an object comprising at least one apparatus for receiving and positioning an object according to claim 1, the arrangement further comprising a gripper having at least one gripper arm (16*a*,16*b*) for gripping the object and for placing the object on or picking the object up from the support surface (3) with simultaneous actuation of the lever (12).

8. The arrangement of claim 7, wherein the gripper arm comprises two parallel gripper arms which together are raised and lowered and are moved parallel to the plane of the support surface (3), the two gripper arms being movable toward and away from each other.

9. The arrangement of claim 7, wherein the lever (12) further comprises a surface (13) adapted to be pressed by the at least one gripper arm (16*a*) for causing the clamping plate (10) to be drawn back from a starting position, facilitating deposition of an object on the support surface (3) and the surface further adapted to be released by the at least one arm (16*a*) for causing the clamping plate (10) to be moved toward the starting position until it abuts the object and pushes the object toward the stop in the form of fins (4*b*,4*c*), and presses the object against the fins in an exactly defined position.

* * * * *

UNITED STATES PATENT AND TRADEMARK OFFICE
CERTIFICATE OF CORRECTION

PATENT NO.   : 6,514,465 B2
DATED        : February 4, 2003
INVENTOR(S)  : N. Ingenhoven It is certified that error appears in the above-identified patent and that said Letters Patent is hereby corrected as shown below:

<u>Title page, Item [54], and Column 1, Line 3,</u>
Please change "AND" (first occurrence) to -- AN --.

Signed and Sealed this

Twenty-second Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,514,465 B2  Page 1 of 1
DATED : February 4, 2003
INVENTOR(S) : Edwin Steiner It is certified that error appears in the above-identified patent and that said Letters Patent is hereby corrected as shown below:

<u>Title page, Item [54], and Column 1, Line 3,</u>
Please change "AND" (first occurrence) to -- AN --.

This certificate supersedes Certificate of Correction issued July 22, 2003.

Signed and Sealed this

Thirtieth Day of March, 2004

JON W. DUDAS
*Acting Director of the United States Patent and Trademark Office*

UNITED STATES PATENT AND TRADEMARK OFFICE
CERTIFICATE OF CORRECTION

PATENT NO.    : 6,514,465 B2
DATED         : February 4, 2003
INVENTOR(S)   : Steiner It is certified that error appears in the above-identified patent and that said Letters Patent is hereby corrected as shown below:

<u>Title page, Item [54], and Column 1, Line 3,</u>
Please change "AND" (first occurrence) to -- AN --.

This certificate supersedes Certificate of Correction issued July 22, 2003.

Signed and Sealed this

Sixth Day of April, 2004

JON W. DUDAS
*Acting Director of the United States Patent and Trademark Office*